(12) United States Patent  
Bouton

(10) Patent No.: US 11,771,895 B2
(45) Date of Patent: Oct. 3, 2023

(54) COMPACT AURICULAR STIMULATION DEVICE

(71) Applicant: The Feinstein Institutes for Medical Research, Manhasset, NY (US)

(72) Inventor: Chad Edward Bouton, Darien, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 0 days.

(21) Appl. No.: 17/394,453

(22) Filed: Aug. 5, 2021

(65) Prior Publication Data

US 2022/0040480 A1 Feb. 10, 2022

Related U.S. Application Data

(60) Provisional application No. 63/062,007, filed on Aug. 6, 2020.

(51) Int. Cl.
*A61N 1/36* (2006.01)
*A61N 1/375* (2006.01)

(52) U.S. Cl.
CPC ..... *A61N 1/36036* (2017.08); *A61N 1/36014* (2013.01); *A61N 1/375* (2013.01)

(58) Field of Classification Search
CPC .. A61N 1/0456; A61N 1/0472; A61N 1/0484; A61N 1/36014; A61N 1/36036
See application file for complete search history.

(56) References Cited

U.S. PATENT DOCUMENTS 5,514,175 A 5/1996 Kim et al.
7,856,275 B1 * 12/2010 Paul ................... A61N 1/36014
607/55

(Continued)

FOREIGN PATENT DOCUMENTS

WO 2017091705 6/2017
WO 2017120023 7/2017

(Continued)

OTHER PUBLICATIONS

International Search Report and Written Opinion for PCT/US2021/044583 dated Nov. 9, 2021.

(Continued)

*Primary Examiner* — Eric D. Bertram
(74) *Attorney, Agent, or Firm* — Wissing Miller LLP

(57) ABSTRACT

Disclosed are nerve stimulation assemblies adapted to apply stimulation signals to a person's nervous system. The assemblies are adapted to apply such signals to nerves terminating on the outer ear of a person, for example, the auricular branch of the vagus nerve. The assemblies comprise an ear canal extension adapted to fit within an ear canal of the person, a housing connected with the extension, and an electrode arm connected with the housing by a connection member. The connection member is adapted to articulate the electrode arm to position the electrode arm relative to the outer ear. An electrode is connected with a distal end of the arm. When the arm is articulated to a selected orientation and the extension is fitted in the ear canal, the electrode is in electrical contact with a portion of the outer ear innervated by a selected peripheral nerve, such as the vagus nerve.

23 Claims, 9 Drawing Sheets

(56) References Cited

U.S. PATENT DOCUMENTS

| | | | |
|---|---|---|---|
| 9,415,220 B1 | 8/2016 | Spinelli et al. | |
| 9,782,584 B2 | 10/2017 | Cartledge et al. | |
| 10,039,928 B2* | 8/2018 | Hyde | A61H 23/0245 |
| 10,130,809 B2 | 11/2018 | Cartledge et al. | |
| 10,279,178 B2 | 5/2019 | Cartledge et al. | |
| 10,327,984 B2* | 6/2019 | Goodall | A61N 2/002 |
| 2003/0195588 A1* | 10/2003 | Fischell | A61N 2/02 |
| | | | 607/55 |
| 2005/0165460 A1* | 7/2005 | Erfan | A61N 1/0472 |
| | | | 607/57 |
| 2008/0021517 A1* | 1/2008 | Dietrich | H04R 25/00 |
| | | | 607/57 |
| 2010/0198282 A1* | 8/2010 | Rogers | A61F 7/007 |
| | | | 607/3 |
| 2015/0165195 A1* | 6/2015 | Hartlep | A61N 1/3603 |
| | | | 607/62 |
| 2016/0279435 A1* | 9/2016 | Hyde | A61N 7/00 |
| 2016/0360970 A1* | 12/2016 | Tzvieli | A61B 5/0075 |
| 2017/0027812 A1* | 2/2017 | Hyde | G16H 10/20 |
| 2017/0087364 A1* | 3/2017 | Cartledge | A61N 1/36034 |
| 2017/0113042 A1* | 4/2017 | Goodall | A61N 5/0622 |
| 2017/0368329 A1* | 12/2017 | Tyler | G10L 15/02 |
| 2018/0339148 A1* | 11/2018 | Kong | A61N 1/37 |
| 2019/0275322 A1 | 9/2019 | Cartledge et al. | |
| 2019/0351230 A1 | 11/2019 | Cartledge et al. | |
| 2021/0085974 A1* | 3/2021 | Bouton | A61B 5/4836 |

FOREIGN PATENT DOCUMENTS

| | | |
|---|---|---|
| WO | 2020068830 | 4/2020 |
| WO | 2020198453 | 10/2020 |

OTHER PUBLICATIONS

DyAnsys Develops Non-Narcotic Solution for Patients with Long-Term Chronic Pain, May 19, 2015, pp. 1-12.

Sabine M. Sator-Katzenschlager et al., P-Stim Auricular Electoacupunture Stimulation Device for Pain Relief, Device Profile, Expert Rev. Med. Devices 4(1), pp. 23-32 (2007).

P-Stim/HRV Testing for the Treatment of Chronic Pain, DyAnsyn Inc., 1 page.

Sabine M. Sator-Katzenschlager et al., The Short and Long Term Benefit of Chronic Low Back Pain Through Adjuvant Electrical Versus Manual Auricular Acupuncture, Department of Anesthesiology and Intensive Care Medicine(B), Outpatient Pain Center, the Department of Vascular Surgery, the Ludwig Boltzmann Institute of Consciousness Psycology and Transculture Psychotherapy, and the Department of Medical Computer Science, University of Vienna, Austria, InternationalAnesthesia Research Society, 2004, vol. 98, pp. 1359-1364.

Sabine M. Sator-Katzenschlager et al., Electrical Stimulation of Auricular Acupuncture Points is More Effective Thank Conventional Manual Auricular Acupuncture in Chronic Cervical Pain: A Pilot Study, Department of Anesthesiology and Intensive Care B, Outpatient Pain Center, Department of Vascular Surgery, and Department of Medical Computer Science, University of Vienna, Vienna, Austria, International Research Society, 2003, vol. 97, pp. 1469-1473.

Medical Policy Manual, Auricular Electrostimulation, Medicine, Policy No. 146, BridgeSpan, May 1, 2019, pp. 1-4.

Huang, F. et al. Effect of 6 transcutaneous auricular vagus nerve stimulation on impaired glucose tolerance: A pilot randomized study. BMC Complementary and Alternative Medicine, (2014), pp. 1-8, https://doi.org/10.1186/1472-6882-14-203.

Schukro, RP. et al., The effects of auricular electroacupuncture on obesity in female patients—a prospective randomized placebo-controlled pilot study. Complementary therapies in medicine. Feb. 2014;22(1):21-5. PMID: 24559812.

Holzer, A. et al. Auricular acupuncture for postoperative pain after gynecological surgery: a randomized controlled trail. MinervaAnestesiol, Mar. 2011; 77(3):298-304. PMID: 21441884.

Bernateck, M. et al., Adjuvant auricular electroacupuncture and autogenic training in rheumatoid arthritis: a randomized controlled trial. Auricular acupuncture and autogenic training in rheumatoid arthritis, Forsch Komplementmed. Aug. 2008;15(4):187-93. PMID: 18787327.

Stefan, H., Epilepsia vol. 53, Issue 7, Brief Commuication, Transcutaneous Vagus Nerve Stimulation (t-VNS) in Pharmacoresistant epilepsies: A Proof of Concept Trial, May 3, 2012, pp. 1-8.

Badran, B.W., Tragus or cymba conchae, Investigating the Anatomical Foundation of Transcutaneous Auricular Vagus Nerve Stimulation (taVNS), HHS Public Access Author Manuscript Brain Stimul. Author manuscript; available in PMC 2019, Published in final edited form as: Brain Stimul. 2018 ; 11(4): 947-948. doi: 10.1016/j.brs.2018.06.003, pp. 1-4.

Clancy, Jennifer A., et al. "Non-invasive vagus nerve stimulation in healthy humans reduces sympathetic nerve activity." Brain stimulation 7.6 (2014): 871-877.

Mercante, B. et al., Medicines, Auricular Neuromodulation: The Emerging Concept Beyond the Stimulation of Vagus and Trigeminal Nerves, Published Jan. 21, 2018,pp. 1-15.

\* cited by examiner

COMPACT AURICULAR STIMULATION DEVICE

CROSS-REFERENCE TO RELATED APPLICATIONS

The present disclosure is based on and claims benefit from U.S. Provisional Patent Application Ser. No. 63/062,007, filed on Aug. 6, 2020, entitled "Compact Auricular Stimulation Device" the contents of which are incorporated herein in their entirety by reference.

BACKGROUND

Field

This disclosure relates to systems, apparatuses, applications, and methods to deliver electrical stimulation to a patient's peripheral nervous system. More particularly, the disclosure relates to a device that is adapted to fit onto a person's outer ear and that includes an electrode positioned in contact with a portion of the ear innervated by the vagus or trigeminal nerve, where the electrode can be adjusted to customize the device to the patient's anatomy.

Transcutaneous auricular stimulation has been studied in many clinical applications ranging from diabetes (Huang et al., 2014) to epilepsy treatment (Stefan et al., 2012). The technique uses electrodes in contact with selected areas on a person's outer ear connected with an electrical waveform generator. Nerve stimulation current is applied to nerves that terminate in the outer ear to stimulate activity in the patient's peripheral nervous system. This stimulation may induce changes to the person's body that have beneficial health effects.

In order to ensure nerve stimulation signals delivered to the selected nerve, electrodes need to be accurately located relative to the person's anatomy. For example, to apply stimulation to the vagus nerve via the ear, an electrode needs to be placed in contact with the cymba concha of the outer ear where the auricular branch of the vagus nerve terminates. To apply stimulation to the trigeminal nerve via the ear, an electrode needs to be positioned near the crus of helix of the ear. Electrodes also need to have a relatively low impedance connection to the person's tissue to ensure that sufficient stimulation current passes through the targeted nerve.

One way to provide transcutaneous auricular nerve stimulation is to attached individual electrodes to the person's outer ear using an adhesive. Adhesive electrodes may need to be positioned by a health professional to assure they are accurately positioned relative to the patient's anatomy. Even if a health professional is not required, it may be difficult for a person to apply an adhesive electrode without assistance.

A device that fits over the auricle of the outer ear or that engages the ear canal may be used to position an electrode against the person's tissue to provide nerve stimulation. One problem that may arise is that the anatomy of the human outer ear varies from person to person. To assure that the electrode of such a device is properly positioned may require adjustment of the device. It may be difficult for a person to know if the electrode is properly positioned and that the device is in good electrical contact with the correct tissue to provide the intended nerve stimulation.

SUMMARY

The present disclosure relates to apparatuses and methods to address these difficulties.

According to one aspect of the disclosure, there is provided an electrode assembly for applying transcutaneous nerve stimulation to a person's outer ear that includes a housing with an extension that fits within the person's ear canal and an articulable arm holding a stimulation electrode. The arm is adjustable, allowing the person to reposition the arm to put the electrode in contact with a selected part of the ear to provide stimulation to a selected peripheral nerve. The arm may rotate about one, two or three axes with respect to the housing and may extend and retract to accommodate differences in outer ear anatomy. According to a further aspect, instead of a rotating/extending arm, an electrode may be provided on a bendable gooseneck that can be repositioned and that holds the electrode securely.

According to another aspect, a pair of electrode assemblies are provided, one for the right ear and one for the left ear. The assemblies each have a single electrode for providing stimulating current. To reduce contact impedance, the electrodes are adapted to be used with a liquid, semi-liquid, or semi-solid electrolyte material. The electrolyte material provides a low impedance conductive path from the electrode to the person's tissue. The left and right ear assemblies are each connected with a waveform generator so that electrodes on the left and right ear provide an electrical path from the waveform generator through the person's body. Providing a single electrode on each of the patient's ears prevents the electrolyte solution from creating a short circuit path that might otherwise occur if anode and cathode electrodes are provided in close proximity on or near the same one of the person's ears.

According to another aspect, the disclosure provides an assembly including an arm for positioning a nerve stimulation electrode to stimulate a person's vagus nerve by locating the electrode against the person's cymba conchae. According to another aspect, the disclosure provides an assembly for stimulating the trigeminal nerve by positioning an electrode against the person's crus/spin of helix. According to a still further aspect, the same assembly can be adjusted to provide stimulation for either the vagus or trigeminal nerve, or to both the vagus and trigeminal nerves by repositioning the adjustable arm.

According to a still further aspect of the disclosure, the housing holding the ear canal extension and the adjustable electrode arm also includes a speaker adapted to provide sound to the person's ear canal. Entertainment, such as music, may be provided to the person via the speaker. According to another aspect, audible signals may be provided to the user to assist in properly positioning the electrode, for example, by providing a feedback signal indicating when a low impedance contact has been achieved and/or when the proper nerve is being stimulated. According to one embodiment, a feedback signal is generated based on an impedance measurement within a specified range, for example, 1000-5000 ohms.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
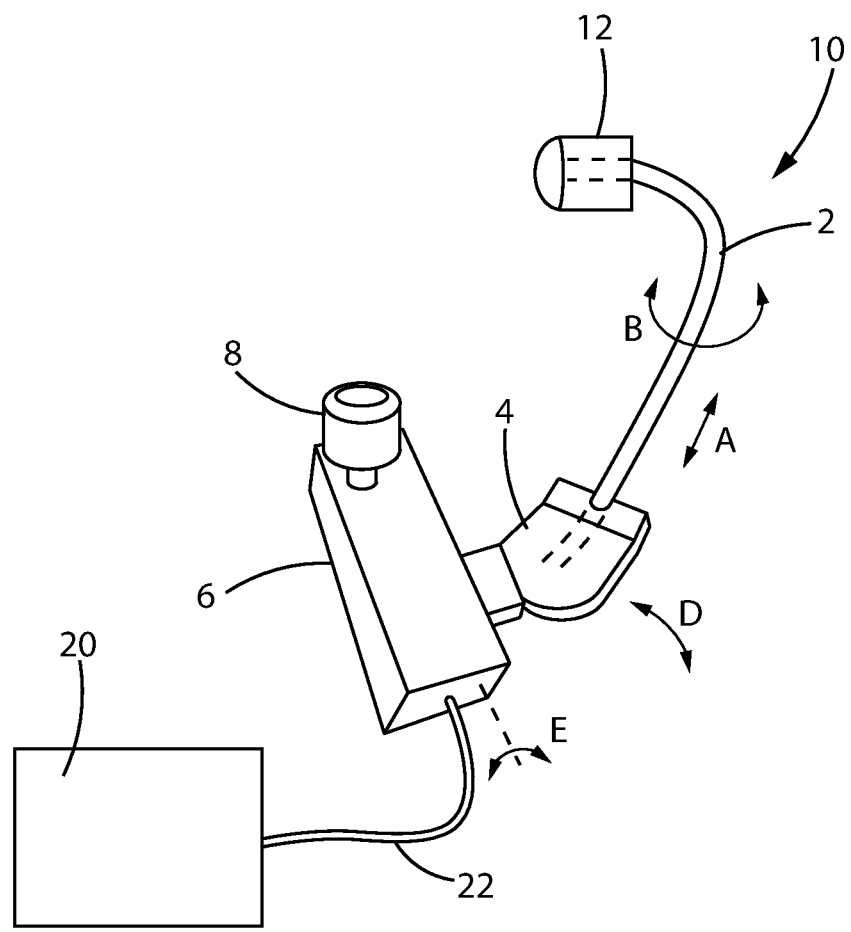
FIG. 1 shows a perspective view of an electrode assembly according to an embodiment of the disclosure.

FIG. 1 shows an electrode assembly 10 according to an embodiment of the disclosure. Housing 6 supports ear canal extension 8. Extension 8 is designed to fit within the ear canal of a person. Extension 8 may include removable/replaceable covers to adjust the diameter of the extension to snugly fit within a person's ear canal.

Housing 6 is connected with connection member 4. Arm 2 is connected with connection member 4. As illustrated by arrow A, according to one embodiment, arm 2 can extend or retract longitudinally with respect to the connection member 4. As illustrated by arrow B, according to a further embodiment, arm 2 can rotate about its longitudinal axis. Connection member 4 may include stops or other mechanisms that limit the amount of rotation shown by arrow B to prevent over-rotation that could damage electrical connections to arm 2.

Connection member 4 is connected with housing 6 by a pivot that allows member 4 to swivel, as shown by arrow D, and also to pitch, as shown by arrow E. The various degrees of freedom illustrated by arrows A, B, C, D, and E allow arm 2 to be positioned to adjust the location of electrode 12. Sufficient friction is provided between housing 6 and member 4 and between member 4 and arm 2, so that, once the assembly is configured by adjusting motion indicated by arrows A-E, arm 2 will stay fixed with respect to housing 6 until force is applied to reconfigure the arm.

An electrode 12 is provided at the distal end of arm 2. Arm 2 and connection member 4 may be formed from a metal or conductive components that provided a conductive path from housing 6 to electrode 12. Alternatively, arm may be formed from a non-conductive material and an electrical conductor such as a wire is provided between housing 6 and electrode 12.

Electrode 12 is designed to provide an electrical connection with the user's skin, and in particular, with the surface of the user's outer ear. Electrode 12 is preferably made from a flexible material to allow it to be comfortably pressed against the user's skin. According to one embodiment, electrode 12 is formed from silicone rubber or other biocompatible material with a softness selected for comfort. According to one embodiment, the soft material comprising electrode 12 has a hardness on the Shore A scale of about 30 to about 50. According to a preferred embodiment, the soft material has a Shore A hardness of about 40. Where the soft material is non-conductive and biocompatible for skin contact applications, such as silicone rubber, a sufficient concentration of conductive particles, such as carbon particles, carbon nanotubes, metal flakes, and the like are embedded in the material to provide electrical conductivity. As will be described more fully below, an electrical waveform applied to electrode 12 via arm 2 is carried through electrode 12 by the conductive particles and into the person's tissue.

To provide nerve stimulation, a relatively low impedance connection needs to be made between electrode 12 and the user's skin. According to one embodiment, the contact between electrode 12 and the user's outer ear is enhanced by applying a conductive liquid or semi-liquid material between electrode 12 and the user's skin to decrease skin impedance and facilitate current flow. This material may be a conductive lotion or an electrode gel, such as Spectra 360® by Parker Laboratories, Inc. According to another embodiment, electrode 12 is a carbon infused open cell foam. To reduce impedance and increase current flow, the foam is saturated with an electrolyte solution, such as saline. According to a still further embodiment, electrode 12 is formed from a solid hydrogel material bonded to the surface of a carbon-loaded silicone rubber core. According to one embodiment, electrode 12 is formed using commercially available hydrogel electrode material, such as AG2540, manufactured by Axelgaard Manufacturing Co. Ltd. According to a still further embodiment, a highly conductive polymer, such as poly(3,4-ethylenedioxythiophene) (PEDOT) forms electrode 12 or is applied to the surface of electrode 12 to enhance a low-impedance connection with the user's skin.

Electrode 12 is fixed to the distal end of arm 2. According to one embodiment, electrode 2 is removable, for example, by being connected with arm 2 via a friction interference fit. According to another embodiment, electrode 12 includes a metal pin or screw that connects with the distal end of arm 2 via a snap fitting or a threaded connection. This allows the electrode 12 to be replaced, for example, when it is worn out or where different users wish to avoid using the same electrode.

According to another embodiment, electrode 12 is provided in a pre-moistened state by being soaked or coated with a conductive lotion, electrode gel, or electrolyte when it is manufactured, and then provide to the user in a seal package, such as a blister pack. By allowing electrode 12 to be removed and replaced, both reusable and disposable electrodes 12 can be used with the assembly.

Waveform generator 20 is connected with housing 6 by a wire 22. Within housing 6, circuitry delivers electrical signals from the waveform generator to electrode 12. The assembly 10 may be worn singly, with electrode 12 in contact with a peripheral nerve on either the right ear or left ear. According to a preferred embodiment, a pair of assemblies 10 are provided, one for the left ear and one for the right ear.

According to a further embodiment, ear canal extension 8 includes an audio speaker. When the assembly is positioned on the outer ear of the person with extension 8 positioned within the person's ear canal, sounds are provided to the person. These may include entertainment, such as music. The sounds may also include feedback signals to assist the person in properly positioning electrode 12 to provide a low-impedance connection to the outer ear. According to a preferred embodiment, ear canal extension 8 is formed from an insulator, such as silicone rubber without conductive particles. This insulation electrically isolates housing 6 from the stimulation signal applied by electrode 12 and limits leakage of the stimulation signal back to the housing and may increase the current applied to person's innervated tissue to improve nerve stimulation.

Figure 2:
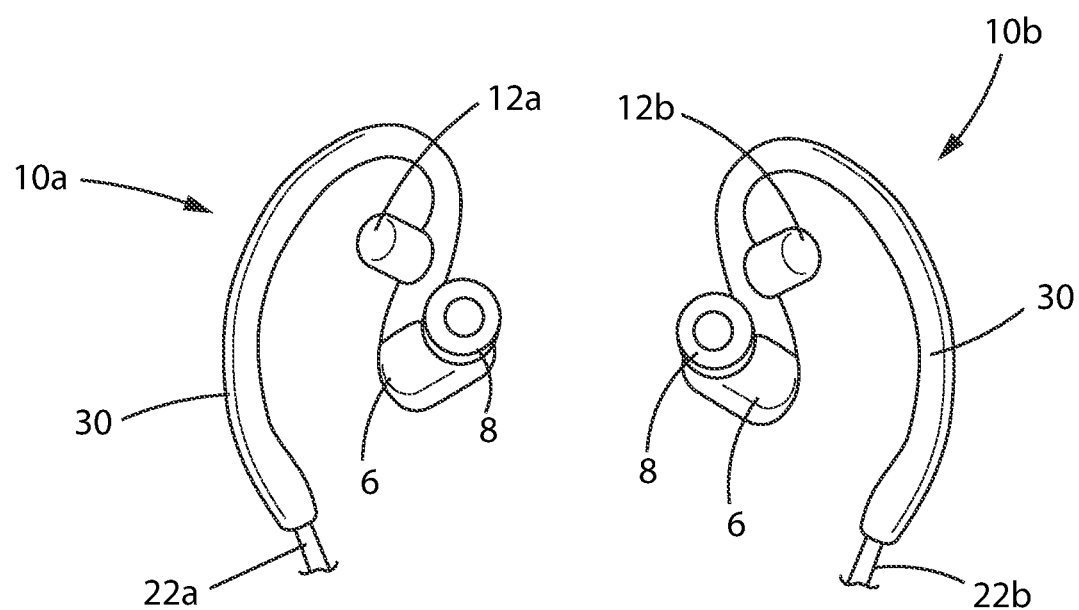
FIG. 2 shows an electrode assembly according to another embodiment of the disclosure.
Figure 4:
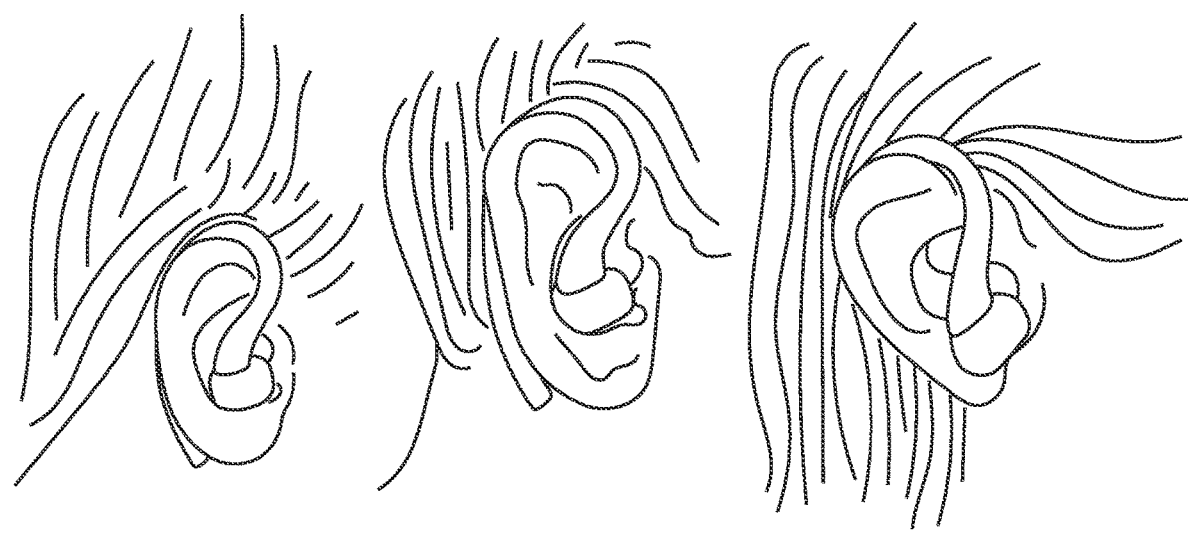
FIG. 4 shows an electrode assembly according to an embodiment of the disclosure adjusted to fit the outer ear of persons with different outer ear anatomy.

FIG. 2 shows left and right electrode assemblies 10a, 10b according to a further embodiment of the disclosure. The same element numbering has been used as in the embodiment of FIG. 1 to show similar structures. In this embodiment, a pair of assemblies is provided. The assemblies 10a, 10b are each shaped to fit onto the persons' respective left and right outer ear. The assemblies 10a, 10b include a housing 6 with an ear canal extension 8 and an over-ear support 30. As shown in FIG. 4, the over-ear support 30 secures each assembly 10a, 10b to the back of the person's respective auricle. This provides a more secure engagement of the assembly with the ear. Electrodes 12a and 12b are connected to their respective housings 6 by an arm. In this embodiment a resilient coating is applied over the arm holding the electrode 12a, 12b as well as over support 30. In the view of FIG. 2, the coating obscures the arm. The resilient coating is sufficiently flexible that the arm can be adjusted, as discussed in the previous embodiment to adjust the position of electrode 12a, 12b with respect to the person's ear. The resilient coating may be formed from a non-conductive material to prevent dissipation of current from the respective electrode to its respective housing 6 and may increase current flowing between electrodes 12a, 12b and hence, the stimulation current flowing through the person's innervated tissue. According to a preferred embodiment, the resilient coating is a non-conductive silicone rubber. As with the previous embodiment, electrode 12a, 12b may be formed from a solid hydrogel material bonded to the surface of a carbon-loaded silicone rubber core. According to one embodiment, using the structure shown in FIG. 2, electrodes 12a, 12b including commercially available hydrogel electrode material, such as AG2540, manufactured by Axelgaard Manufacturing Co. Ltd. and provides skin impedance values from 4000-6000 ohms using a 10 kHz sinusoidal test waveform.

Figure 3A:
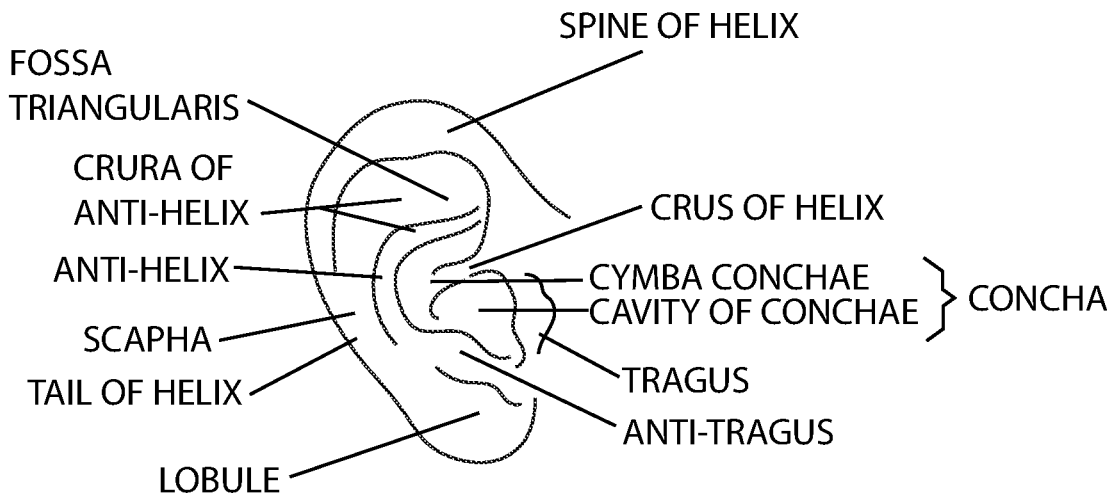
FIGS. 3a and 3b illustrate the anatomy of the human outer ear relative to terminations of the vagus and trigeminal nerves.
Figure 3B:
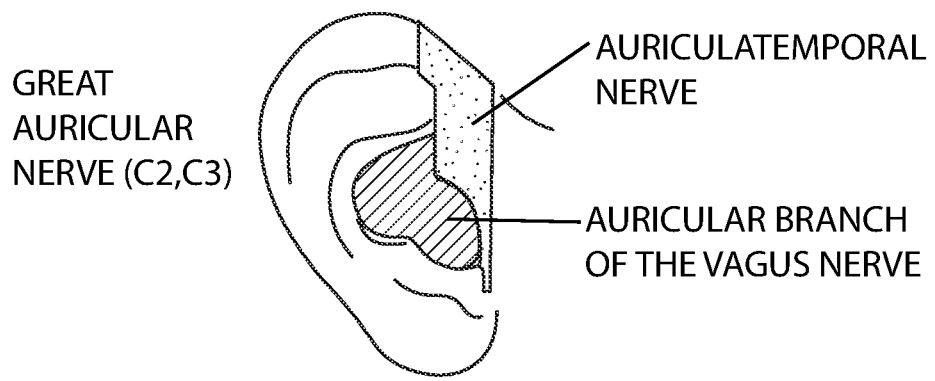

FIGS. 3a and 3b show the anatomy of the human outer ear. As shown in FIG. 3b, the auricular branch of the vagus nerve terminates in a region adjacent and dorsal of the ear canal that includes the cymba concha. The auriculotemporal branch of the trigeminal nerve terminates in a region ventral and superior to the ear canal and includes the crus of helix of the outer ear. The vagus and auriculotemporal nerves are peripheral nerves that connect with portions of the central nervous system (CNS) that control hormonal, circulatory, respiratory, and digestive activity.

FIG. 4 shows an assembly according to the embodiment illustrated in FIG. 2 positioned on three human subjects. Ear canal extension 8 is fitted within the subject's ear canal and over-ear support 30 is fitted behind the outer ear auricle. Because the anatomy of the outer ear varies from person to person, the assembly is adjusted by repositioning arm 2 with respect to housing 6 so that electrode 12 is pressed against a selected region of the outer ear (e.g., the cymba conchae to stimulate the vagus nerve). In this configuration, electrical signals applied to electrode 12 are communicated to the vagus nerve. Arm 2 can be repositioned by moving it as indicated by arrows A-E shown in FIG. 1 to contact the crus of helix to contact auriculotemporal branch of the trigeminal nerve or to contact tissue between the crus of helix and cymba conchae innervated by both the vagus and trigeminal nerves.

Figure 8A:
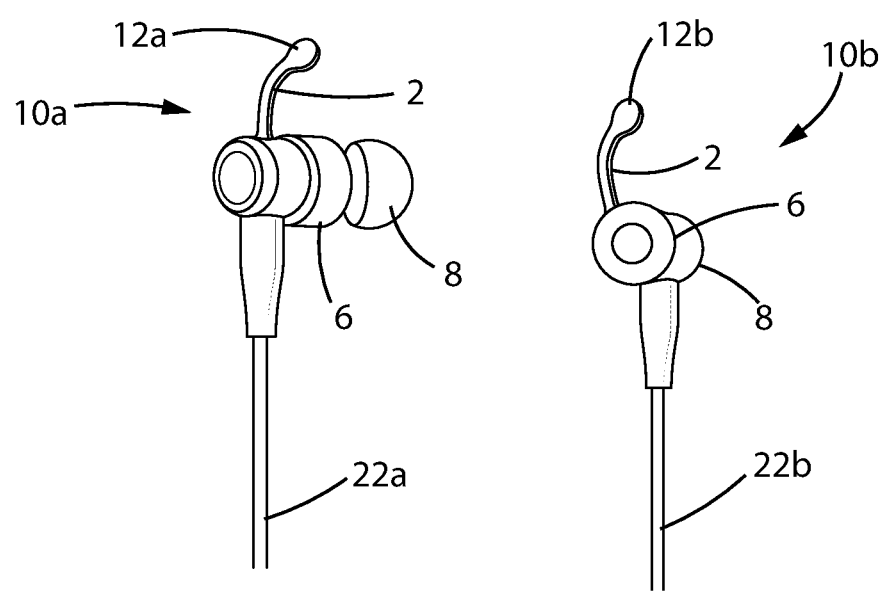
FIGS. 8a and 8b show a perspective view of an electrode assembly according to a still further embodiment of the disclosure and the placement of the assembly in the outer ear of a person.
Figure 8B:
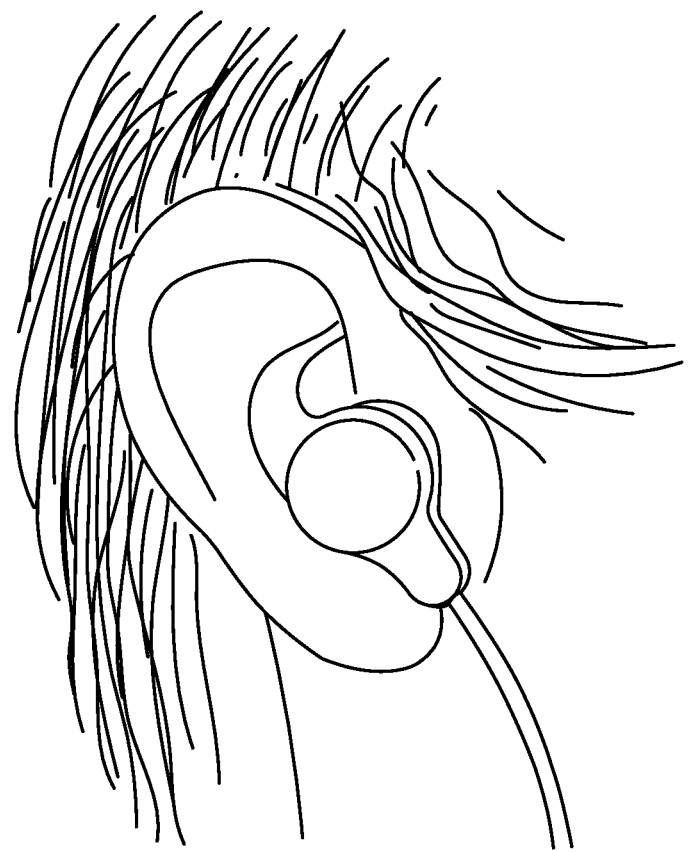

FIG. 8a shows a pair of left and right assemblies 10a, 10b according to an alternative embodiment of the disclosure. As with the embodiments described above, ear canal extension 8 extends from housing 6. Arm 2 extends from housing 6 and can be articulated as described with respect to previous embodiments. At the end of arm 2 is electrode 12a, 12b. FIG. 8b shows the assembly of FIG. 8a positioned onto a person's outer ear. Arm 2 is adjusted to position electrodes 12a, 12b in contact with portions of the person's left and right outer ear innervated with a target nerve, for example, the vagus nerve.

Figure 5:
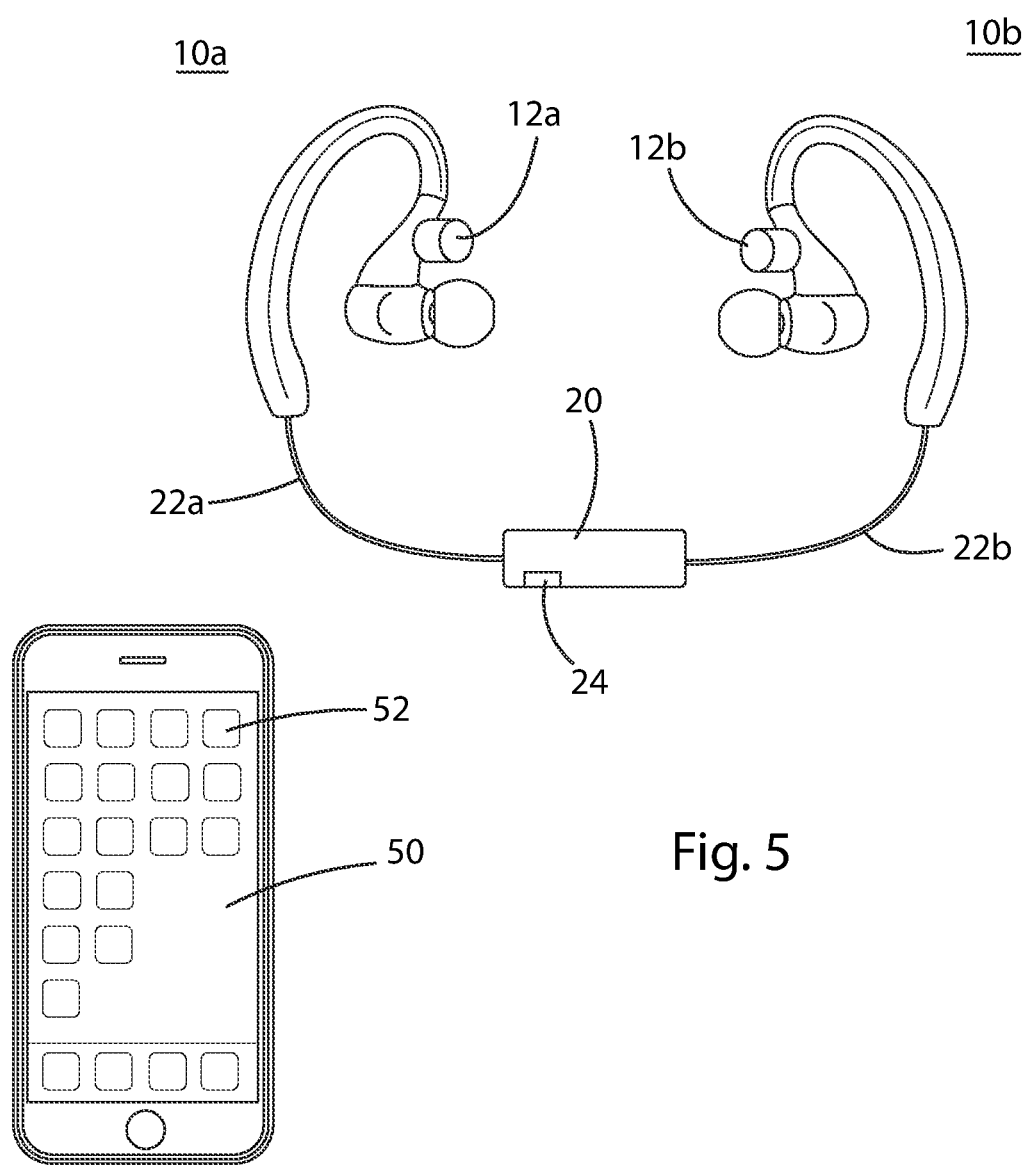
FIG. 5 shows an electrode assembly according to yet another embodiment of the disclosure.

FIG. 5 shows a pair of electrode assemblies 10a, 10b according to another embodiment of the disclosure. The pair of electrode assemblies 10a, 10b are shaped to fit onto the left and right outer ear of the person. The assemblies 10a, 10b are connected with a waveform generator 20 by wires 22a, 22b. The generator 20 includes a wireless communication device 24, such as a Bluetooth transceiver or a ZigBee transceiver. A controller 50 is located in proximity to the generator 20. Controller 50 also includes a wireless communication device 52 adapted to communicate with device 24 of generator 20. The controller 50 could be a custom-made device designed specifically to work with assemblies 10a, 10b and generator 20. Alternatively, controller 50 is a general-purpose device such as a cellular telephone that includes an application allowing it to interact with and control generator 20, for example, using a Bluetooth protocol. According to one embodiment, generator 20 includes an attachment to comfortably and stably connect it with the persons clothing or to their body, such as by a hook, a belt clip, a lanyard, an arm band, or the like. Wires 22a, 22b are sufficiently long to accommodate connection of generator 20. This arrangement allows a device according to the disclosure to be worn while the person engages in physical activities, for example, walking, jogging, running, and the like.

Figure 6A:
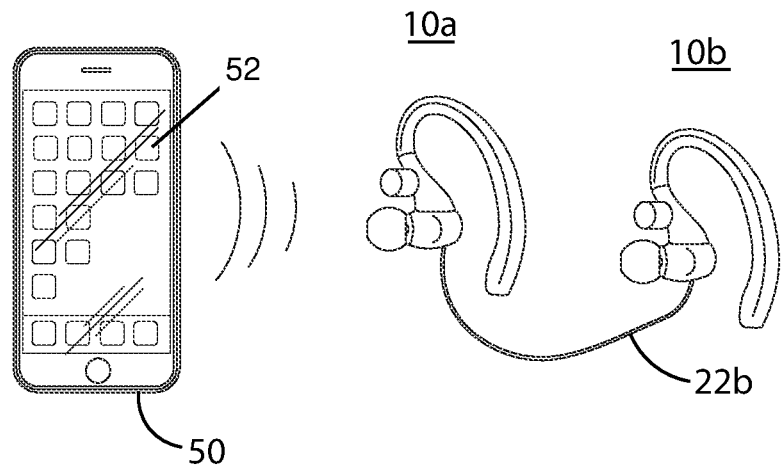
FIGS. 6a and 6b show a perspective view of an electrode assembly according to yet another embodiment of the disclosure and a block diagram illustrating an arrangement of components according to that embodiment.
Figure 6B:
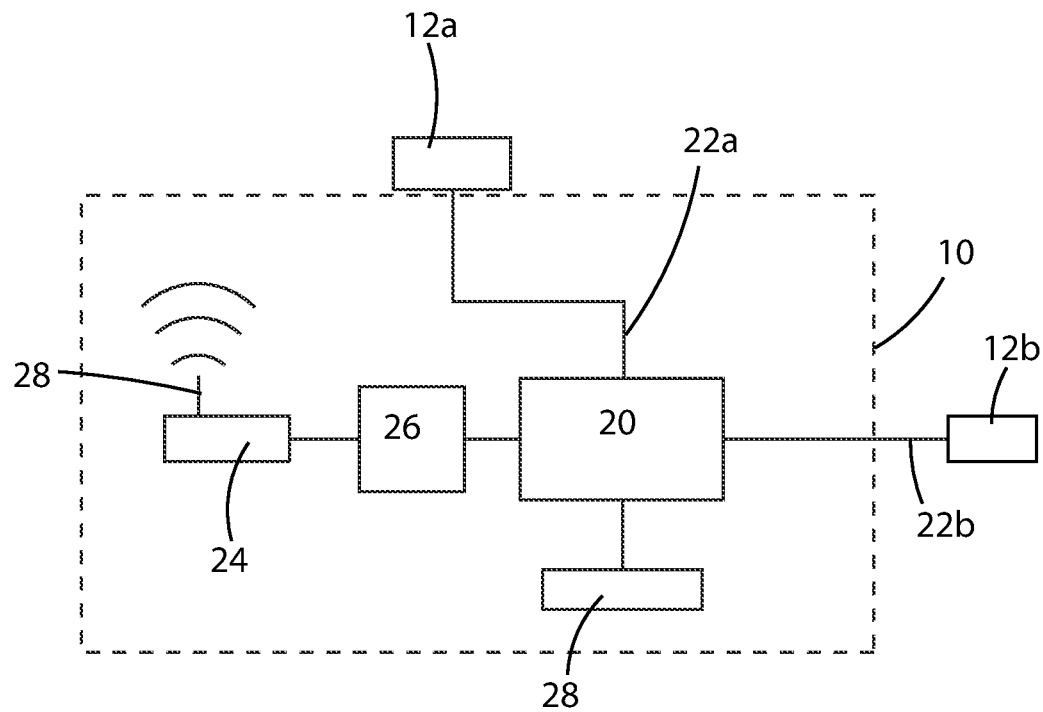

FIGS. 6a and 6b show yet another embodiment of the disclosure. One or two assemblies 10a, 10b are provided. These assemblies may be configured as shown in the embodiments of FIG. 1, 2, or 8a. Controller 50, such as a cellular phone, is provided in proximity to assemblies 10a, 10b. Controller 50 includes a wireless communication device 52 and software that allows it to interact with and control assemblies 10a, 10b. Assemblies 10a, 10b are connected with one another by wire 22b to deliver a stimulation waveform signal, in opposite polarity, to electrodes 12a and 12b positioned on the opposite ears. As shown in FIG. 6b, circuitry is provided, for example, within assembly 10a (or alternatively assembly 10b) to deliver electrical stimulation signals to electrode 12a (with wire 22a remaining contained within the 10a assembly) and to deliver electrical stimulation signals through wire 22b to electrode 12b. According to one embodiment, this circuitry includes a waveform generator 20 and a power supply 28 such as a rechargeable battery to provide sufficient energy to the generator 20 to deliver nerve stimulation signals. Processor 26 is connected with generator 20. Processor 26 provides signals to the generator 20 that define characteristics of the stimulus signal. These characteristics describe voltage or current of the signal and may include the amplitude, polarity, frequency, wave shape, pulse duration, pulse width, burst duration, inter-burst rest period and other signal characteristics. The preferred shape of the waveform is sinusoidal, but may be square, triangular, or other shapes. According to one embodiment, the waveform can be monophasic, bi-phasic, or have a complex waveform. According to one embodiment, the signal sent to the left and right ear assemblies 10a, 10b are selected to be of opposite polarities. The electrodes 12a, 12b then become alternating anode and cathode pairs that excite innervated tissues on the right and left ear.

Processor 26 is connected with a transceiver 24 and antenna 28. Radio signals from controller 50 received via antenna 28 are decoded by the processor 26 and used to set the stimulation produced by generator 20.

Figure 7A:
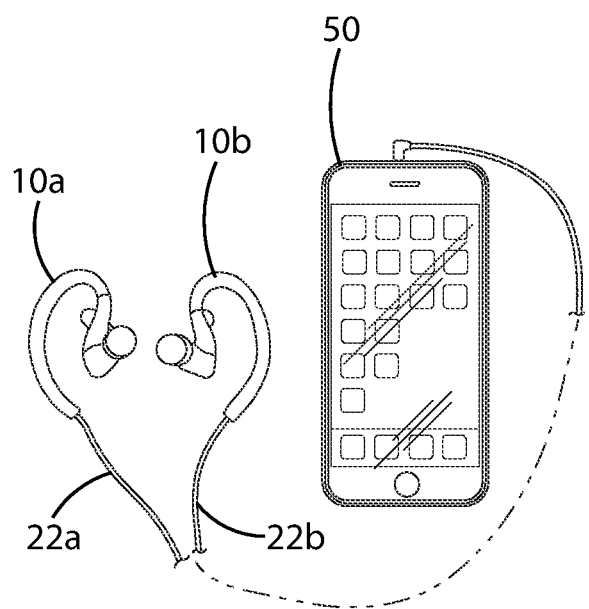
FIGS. 7a and 7b show a perspective view of an electrode assembly according to yet another embodiment of the disclosure and a block diagram illustrating an arrangement of components according to that embodiment.
Figure 7B:
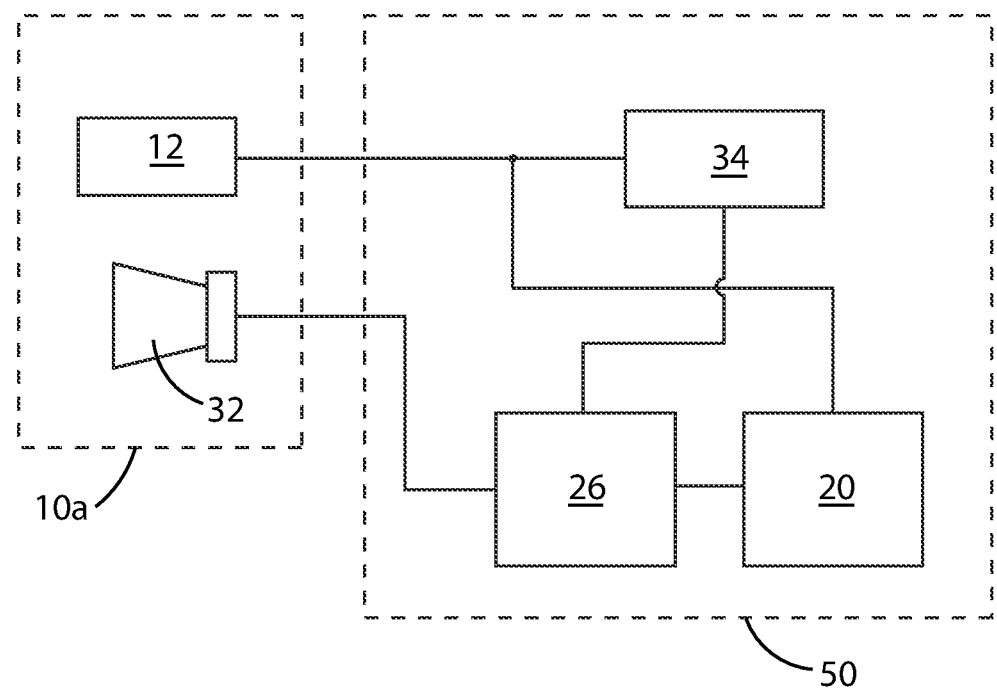

FIGS. 7a and 7b show a nerve simulation system according to a further embodiment of the disclosure. As shown in FIG. 7a, a pair of electrode assemblies 10a, 10b are provided. As shown in the block diagram in FIG. 7b, each assembly 10a, 10b includes a nerve stimulation electrode 12 adapted to stimulate a selected nerve ending using, for example, the structures illustrated in FIGS. 1, 2 and/or 8a. An audio speaker 32 is provided in either or both of the assemblies 10a, 10b. Speaker 32 may be positioned within ear canal extension 8 to project sounds into the person's ear canal. Alternatively, speaker 32 may be a bone conduction speaker in contact with the person's skeletal system to provide audio signals to the person. As with previous embodiments, electrode 12 is connected with a waveform generator 20 to provide a nerve stimulation signal to, for example, the person's vagus or trigeminal nerve.

Also connected with electrode 12 is an impedance detector 34. Impedance detector 34 provides a test signal to electrode 12 and monitors the absorption of the test signal by the person's tissues to determine the contact impedance between electrode 12 and the person's outer ear. Impedance detector 34 measures characteristics of the signal applied by electrode 12, including voltage, current, and phase shift to determine whether a low-impedance contact is made with the person's tissue. According to one embodiment, the test signal includes multiple frequency signals across the range of frequencies that will be used for nerve stimulation. Impedance detector 34 is connected with processor 26. Processor 26 provides an audible signal to the person via speaker 32 that indicates whether a low-impedance connection has been made with electrode 12. According to one embodiment, processor 26 generates a tone with a frequency that is modulated by the contact impedance. According to another embodiment, processor 26 generates a synthesized voice to inform the person when electrode 12 is in proper or improper contact and to inform the user if a low-impedance connection has been lost, for example, because the device has become displaced relative to the person's ear.

Connections between electrode assemblies 10a, 10b and controller 50 may be via wires 22a, 22b, as shown in FIG. 7a. Alternatively, assemblies 10a, 10b may communicate with controller wirelessly, for example, by radiofrequency signals, infrared signals and the like. According to this embodiment, waveform generator 20, impedance detector 34, and processor 26 are housed in housing 6 of one or the other of assemblies 10a and 10b, along with a suitable power source, for example, a rechargeable battery.

According to another embodiment, electrode 12 receives electrical signals generated by the person's body, including signals that show activity of the circulatory system, that is, electrocardiography (ECG) signals. ECG information can be used as bio-feedback during or after stimulation. Processor 26 analyzes the electrical signals received via electrodes 12 to determine the effect of stimulation signals on the person's body, such as changes in the ECG signal. ECG related information can also be sent to the mobile device via the wireless connection.

Heart rate variability (HRV), in particular, has been shown to change during and after auricular vagus nerve stimulation. Spectral analysis of the inter-beat interval has been used to reveal changes in HRV that occur due to the stimulation. See Clancy, Jennifer A. et al. "Non-invasive vagus nerve stimulation in healthy humans reduces sympathetic nerve activity." Brain stimulation 7.6 (2014): 871-877). Specifically, a decrease in the low frequency to high frequency component ratio of the HRV can be used to confirm correct placement and stimulation. According to one embodiment, processor 26 and/or controller 50 includes circuitry and/or software for analyzing HRV and for generating a feedback signal to indicate correct placement of electrodes 12 relative to the person's tissues.

While illustrative embodiments of the disclosure have been described and illustrated above, it should be understood that these are exemplary of the disclosure and are not to be considered as limiting. Additions, deletions, substitutions, and other modifications can be made without departing from the spirit or scope of the disclosure. Accordingly, the disclosure is not to be considered as limited by the foregoing description.

I claim:

1. A nerve stimulation apparatus comprising;
    a pair of nerve stimulation assemblies, each assembly comprising:
        an ear canal extension adapted to fit within an ear canal of an organism;
        a housing connected with the extension;
        an electrode arm connected with the housing by a connection member at a proximal end of the arm, wherein the connection member is adapted to articulate the electrode arm to position the electrode arm relative to an outer ear of the organism; and
        a single electrode connected with a distal end of the arm, wherein when the arm is articulated to a selected orientation and the extension is fitted in the ear canal, the electrode is adapted to be in electrical contact with a portion of the outer ear innervated by a peripheral nerve of the organism, and wherein each nerve stimulation assembly is electrically isolated from the organism except for the single electrode; and
    a nerve stimulation circuit that is electrically connected with the single electrodes of each of the pair of stimulation assemblies, wherein the circuit generates an electrical stimulation signal and delivers the electrical stimulation signal across the single electrodes of each assembly, and wherein the stimulation signal comprises a waveform applied across the single electrodes of the pair of respective assemblies and, for at least a portion of the waveform, a selected first one of the electrodes is at a different voltage relative to a selected second one of the electrodes.

2. The apparatus of claim 1, wherein the ear canal extension is not connected with the stimulation circuit.

3. The apparatus of claim 1, wherein the ear canal extension comprises an electrical insulator at least where the extension contacts the outer ear when the extension is fitted in the ear canal.

4. The apparatus of claim 1, wherein the electrodes are removably connected with the arms.

5. The apparatus of claim 4, wherein the electrodes are formed from one or more of carbon-loaded silicone rubber, carbon-infused foam, a solid hydrogel, a high conductivity polymer, and a PEDOT coating.

6. The apparatus of claim 1, wherein the electrodes comprise an absorbent material and an electrolyte solution in the absorbent material.

7. The apparatus of claim 1, wherein the arms each comprise a first section extending along a longitudinal axis from the proximal end to a bend and a second section extending from the bend to the distal end and wherein the connection member is adapted to allow rotation of the arm about the longitudinal axis relative to the housing.

8. The apparatus of claim 7, wherein the connection member is adapted to allow adjustment of the extension of the first section relative to the housing along the longitudinal axis.

9. The apparatus of claim 7, wherein the connection member is adapted to allow an angular adjustment of the longitudinal axis relative to the housing.

10. The apparatus of claim 1, wherein the housing and at least a portion of the arm of each assembly are encased in an elastomeric material.

11. The apparatus of claim 10, wherein the distal portion of the arm connected with the electrode of each assembly is not encased in the elastomeric material, and wherein the elastomeric material is an electrical insulator.

12. The apparatus of claim 1, further comprising an auricle support connected with the housing to each assembly, the auricle support adapted to fit behind the auricle of the organism when the extension is fitted within the ear canal.

13. The apparatus of claim 1, wherein the nerve stimulation circuit comprises two circuits, one disposed in the housing of each assembly.

14. The apparatus of claim 1, wherein the nerve stimulation circuit comprises a radiofrequency communication circuit adapted to receive a nerve stimulation command and to generate the stimulation signal based on the command.

15. The apparatus of claim 14, wherein the radiofrequency communication circuit comprises a Bluetooth transceiver or a ZigBee transceiver.

16. The apparatus of claim 1, wherein the peripheral nerve is the vagus nerve or the auriculotemporal branch of the trigeminal nerve.

17. The apparatus of claim 1, wherein the nerve stimulation circuit further comprises an impedance detector adapted to determine an impedance between the electrode and the outer ear.

18. The apparatus of claim 17, further comprising a feedback signal generator, the generator adapted to provide a feedback signal to the organism based on the impedance detected by the impedance detector.

19. The assemblies of claim 18, wherein the impedance detector further comprises circuitry for analysing heart rate variability and for generating the feedback signal.

20. The assemblies of claim 1, further comprising an audio signal source adapted to deliver an audible signal to the organism.

21. A system for stimulating nerve tissue in a human comprising:
    left and right nerve stimulation assemblies, each assembly adapted to fit onto the respective left and right ear of the human, each assembly comprising:
    an ear canal extension adapted to fit within the respective left and right ear canal of the human;
    a housing connected with the extension; and
    a single electrode connected with the housing and positioned to contact a respective left and right innervated tissue of the human when the ear canal extension is fitted in the respective left and right ear canal of the human, and wherein the nerve stimulation assembly is electrically isolated from the organism except for the single electrode; and
    a waveform generator connected with the electrodes of the left and right nerve stimulation assemblies,
    wherein the waveform generator generates a stimulation waveform and delivers left and right electrical stimulation signals to the respective electrodes of the left and right assemblies based on the waveform and wherein the left and right signals are selected so that a time varying voltage or current corresponding to the waveform is delivered to innervated tissue of both the left and right ear, and wherein for at least a portion of the waveform, a selected first one of the electrodes is at a different voltage relative to a selected second one of the electrodes.

22. The system of claim 21, wherein the left and right electrical stimulation signals have opposing electrical polarities.

23. The system of claim 21, wherein the waveform is monophasic, bi-phasic, or multi-phasic.

* * * * *